United States Patent
Itoh et al.

(10) Patent No.: US 9,144,539 B2
(45) Date of Patent: Sep. 29, 2015

(54) METHIONINASE INHIBITOR AND COMPOSITION AND FOOD OR DRINK CONTAINING THE SAME

(71) Applicant: Lotte Co., Ltd., Tokyo (JP)

(72) Inventors: Satomi Itoh, Saitama (JP); Atsushi Narise, Saitama (JP); Takanori Tsugane, Saitama (JP); Susumu Shimura, Saitama (JP)

(73) Assignee: Lotte Co, Ltd., Tokyo (JP)

( * ) Notice: Subject to any disclaimer, the term of this patent is extended or adjusted under 35 U.S.C. 154(b) by 0 days.

(21) Appl. No.: 14/314,851

(22) Filed: Jun. 25, 2014

(65) Prior Publication Data

US 2014/0308218 A1    Oct. 16, 2014

Related U.S. Application Data

(62) Division of application No. 12/309,645, filed as application No. PCT/JP2007/063908 on Jul. 12, 2007.

(30) Foreign Application Priority Data

Jul. 27, 2006    (JP) .................................. 2006-204494

(51) Int. Cl.
| | | |
|---|---|---|
| A61K 8/49 | (2006.01) | |
| A23L 1/30 | (2006.01) | |
| A61K 8/97 | (2006.01) | |
| A61K 31/192 | (2006.01) | |
| A61K 31/343 | (2006.01) | |
| A61K 31/353 | (2006.01) | |
| A61K 36/185 | (2006.01) | |
| A61Q 11/00 | (2006.01) | |
| A61K 8/368 | (2006.01) | |

(52) U.S. Cl.
CPC ............... *A61K 8/498* (2013.01); *A23L 1/3002* (2013.01); *A61K 8/368* (2013.01); *A61K 8/4973* (2013.01); *A61K 8/97* (2013.01); *A61K 31/192* (2013.01); *A61K 31/343* (2013.01); *A61K 31/353* (2013.01); *A61K 36/185* (2013.01); *A61Q 11/00* (2013.01); *A61K 2800/782* (2013.01)

(58) Field of Classification Search
CPC ........... A23L 1/3002; A61K 2800/782; A61K 31/192; A61K 31/343; A61K 31/353; A61K 36/185; A61K 8/368; A61K 8/4973; A61K 8/498; A61K 8/97; A61Q 11/00
See application file for complete search history.

(56) References Cited

U.S. PATENT DOCUMENTS

| | | |
|---|---|---|
| 5,264,238 A | 11/1993 | Taga et al. |
| 6,391,344 B2 | 5/2002 | Kosaka et al. |
| 6,723,304 B2 | 4/2004 | Stier |

FOREIGN PATENT DOCUMENTS

| | | |
|---|---|---|
| JP | 06-183940 A | 7/1994 |
| JP | 2001-095910 A | 4/2001 |
| JP | 2005-029571 A | 2/2005 |
| JP | 2006-67874 A | 3/2006 |
| JP | 2006-219389 A | 8/2006 |

OTHER PUBLICATIONS

Form PCT/IB/326, Notification Concerning Transmittal of International Preliminary Report on Patentability English Translation, issued Jan. 27, 2009.
Dong et al., "3-Geranyl-4-hydroxy-5-(3'-methyl-2'-butenyl) benzoic Acid as Anti-inflammatory Compound from Myrsine seguinii," Biosci. Biotechnol.Biochem., 63 (9) pp. 1650-1653 1999.
Zhong, X-N. et al., Three Flavonol Glycosides From Leaves of Myrsine Seguinii, Phytochemistry, 1997, vol. 45, No. 5, pp. 943-946.
International Search Report; International Application No. PCT/JP2007/063908; Date: Oct. 16, 2007.

*Primary Examiner* — Sreeni Padmanabhan
*Assistant Examiner* — Jody Karol
(74) *Attorney, Agent, or Firm* — Fishman Stewart Yamaguchi PLLC

(57) ABSTRACT

The invention provides a methioninase inhibitor to suppress the production of methyl mercaptan that is a causative substance of a bad smell by inhibiting methioninase originated from bacteria, as well as a composition and a food or drink containing the same, wherein the methioninase inhibitor contains an extract obtained from a plant of the family Myrsinaceae, genus *Myrsine*, preferably *Myrsine seguinii* as an active ingredient; and further provides a methioninase inhibitor, as well as a composition and a food or drink containing the same, wherein the methioninase inhibitor contains as an active ingredient one or more selected from the group consisting of myrsinoic acid A, myrsinoic acid B, myrsinoic acid C, myrsinoic acid E and myrsinoic acid F; preferably the myrsinoic acid A, myrsinoic acid B, myrsinoic acid C, myrsinoic acid E and myrsinoic acid F are obtained from a plant of the family Myrsinaceae, genus *Myrsine*, preferably *Myrsine seguinii*.

16 Claims, No Drawings

METHIONINASE INHIBITOR AND COMPOSITION AND FOOD OR DRINK CONTAINING THE SAME

CROSS REFERENCE TO RELATED APPLICATIONS

This Application is a Divisional Application of U.S. patent application Ser. No. 12/309,645, filed Nov. 30, 2009, which is a National Stage Application of PCT/JP 2007-063908, filed on Jul. 12, 2007, which claims priority from Japanese Patent Application JP 2006-204494, filed with the Japanese Patent Office on Jul. 27, 2006, the entire contents of which being incorporated herein by reference.

TECHNICAL FIELD

The present invention relates to an inhibitor of methioninase engaged in production of methyl mercaptan that is a causative substance of a bad smell, as well as a composition and a food or drink containing the same.

BACKGROUND ART

The main components of a bad smell from an oral cavity are volatile sulfur compounds, and especially methyl mercaptan is known to have a high correlation with the intensity of bad breath. Methyl mercaptan is generated from food debris, intraoral desquamated epithelial cells and salivary proteins metabolized or decomposed by oral bacteria. Volatile sulfur compounds such as methyl mercaptan are known to have adverse effects, such as inhibition of intraoral synthesis of proteins, inhibition of collagen synthesis, inhibition of growth and division of endothelial cells, and increase of permeability of intraoral mucosa. Consequently inhibition of methyl mercaptan is an important task not only for suppression of the bad breath, but also for prevention of a periodontal disease or maintenance of the human body's internal environment.

Methyl mercaptan is generated from L-methionine, that is an intraoral protein decomposition product, utilized as a substrate, by an oral bacterial enzyme of methioninase (L-methionine-γ-lyase). Among various bacteria present in the human oral cavity, *Fusobacterium nucleatum* and *Porphyromonas gingivalis* have high methioninase activity, and by inhibiting their methioninase activity the generation of methyl mercaptan, a causative substance of bad smell, as well as hydrogen sulfide, ammonia and α-ketobutyrate can be inhibited. Methyl mercaptan is generated also by enteric bacteria, and known as a causative substance of odors of kitchen garbage and feces. Consequently, by inhibiting methioninase, the odors of garbage and feces are expected to be eliminated.

For suppressing the bad breath, there are various methods, such as disinfection of the oral bacteria generating the odor, chemical conversion of the odor substance to an odorless substance, and masking of the odor by a perfume. However, the use of a disinfectant might have an adverse effect by disturbing a balance of an intraoral bacterial flora, and the odor eliminating by chemical conversion or masking does not inhibit generation of the odor itself and the effect does not last long. Meanwhile the methioninase inhibitor of the present invention is safe, inhibits the generation of methyl mercaptan itself and therefore shows high sustainability.

Methioninase inhibitors originated from natural materials, such as a tomato extract and a ginger extract (e.g. Patent Documents 1 and 2), or an extract of Iceland moss, an extract of alkanet, an extract of green tea and the like (e.g. Patent Document 3) have been reported, and their inhibition of the methyl mercaptan production by oral bacteria, such as *Porphyromonas gingivalis* and *Fusobacterium nucleatum*, has been disclosed. Inhibitory activity on the methyl mercaptan production by oral bacteria of a plant belonging to the family Asteraceae, genera *Chrysanthemum, Cynara*, and *Tagetes* (e.g. Patent Document 4), the family Rutaceae, genus *Zanthoxylum* (e.g. Patent Document 5) and a plant essential oil component (e.g. Non-Patent Document 1); and furthermore inhibitory activity on the methyl mercaptan production by oral bacteria of a certain perfume component (e.g. Patent Documents 6 and 7), and α-ketobutyrate and a salt thereof (e.g. Patent Document 8) have been reported. However, none of them are satisfactory in terms of sustainability of the activity and the like.

Meanwhile, myrsinoic acid A, myrsinoic acid B, myrsinoic acid C, myrsinoic acid E and myrsinoic acid F have been identified from *Myrsine seguinii* or *Rapanaea neriifolia*, a plant belonging to the family Myrsinaceae, genus *Myrsine*, which are substances inhibiting cutaneous inflammation (e.g. Non-Patent Documents 2, 3 and 4).

Furthermore, myrsinoic acid A is known to inhibit cutaneous inflammation by inhibiting a DNA polymerase, but its odor eliminating activity has not been disclosed. Methyl esters of myrsinoic acids A, B and C have been identified from *Rapanea unbellata*, a plant of the same genus, but the bioactivities have not been disclosed (e.g. Non-Patent Documents 5 and 6).

Patent Document 1: Japanese Patent Application Laid-Open No. 2002-3353
Patent Document 2: Japanese Patent Application Laid-Open No. 2003-160459
Patent Document 3: Japanese Patent Application Laid-Open No. 2005-162697
Patent Document 4: Japanese Patent Application Laid-Open No. 2002-114660
Patent Document 5: Japanese Patent Application Laid-Open No. 2003-26527
Patent Document 6: Japanese Patent Application Laid-Open No. 2001-348308
Patent Document 7: Japanese Patent Application Laid-Open No. 2002-3369
Patent Document 8: Japanese Patent Application Laid-Open No. H07-138139
Non-Patent Document 1: Tsuneda, F., Journal of Odor Research and Engineering, 2000, Vol. 31 (2), p. 91-96
Non-Patent Document 2: Biosci. Biotechnol. Biochem., 63(9), 1650-1653, 1999
Non-Patent Document 3: Biosci. Biotechnol. Biochem., 66(3), 655-659, 2002
Non-Patent Document 4: Biosci. Biotechnol. Biochem., 67(9), 2038-2041, 2003
Non-Patent Document 5: Biochimicaet Biophysica Acta, 2000 Jun. 1; 1475 (1): 1-4
Non-Patent Document 6: Phytochemistry, 1991; 30 (6): 2019-2023

DISCLOSURE OF THE INVENTION

Problem(s) to be Solved by Invention

An object of the present invention is to provide a methioninase inhibitor, as well as a composition and a food or drink containing the same, which includes a plant extract that has no adverse effect on human bodies and is highly safe, or myrsinoic acids originated from the plant extract, as an active ingredient, and inhibits methioninase originated from bacteria to suppress the production of an odor substance of methyl mercaptan.

Measure for Solving the Problems

To solve the problems the present inventors have directed attention to natural extracts, such as galenicals or herbs, that have been used since ancient times to establish time-tested safety, and carried out inhibition tests using a cell lysate and a live cell suspension originated from *Fusobacterium nucleatum* that is a causative bacterium of bad breath having high methioninase activity, and discovered that an extract obtained from a plant of family Myrsinaceae, genus *Myrsine* has an inhibitory activity against methioninase and that the active ingredient thereof is myrsinoic acids, thereby completing the present invention.

More particularly, the present invention provides a methioninase inhibitor, a composition and a food or drink characterized by containing an extract obtained from a plant belonging to the family Myrsinaceae, genus *Myrsine*, preferably *Myrsine seguinii* belonging to the family Myrsinaceae, genus *Myrsine*, as an active ingredient; a methioninase inhibitor, a composition and a food or drink characterized by containing one or more selected from the group consisting of myrsinoic acid A, myrsinoic acid B, myrsinoic acid C, myrsinoic acid E and myrsinoic acid F as an active ingredient; and the methioninase inhibitor, the composition and the food or drink characterized in that the myrsinoic acid A, myrsinoic acid B, myrsinoic acid C, myrsinoic acid E and myrsinoic acid F are obtained from a plant belonging to the family Myrsinaceae, genus *Myrsine*, preferably *Myrsine seguinii* belonging to the family Myrsinaceae, genus *Myrsine*.

Effect of the Invention

The methioninase inhibitor of the present invention has activity to suppress the production of methyl mercaptan, ammonia and α-ketobutyrate. Consequently, by ingesting orally a food or drink containing the same, or using the same in an oral composition, such as a mouth freshener or a tooth paste, reduction of bad breath, reduction of feces odor and improvement of mouth's and body's internal environment are possible. Additionally the same can be used as an odor inhibitor for the living environment, as for kitchen garbage.

BEST MODES FOR CARRYING OUT THE INVENTION

The present invention will be described in more detail below. Thereby the methioninase inhibitor of the present invention, a composition and a food or drink containing the same as an active ingredient, a process for producing them, and advantages thereof will be described, provided that the present invention be not limited thereto.

Although myrsinoic acid A, myrsinoic acid B, myrsinoic acid C, myrsinoic acid E and myrsinoic acid F (the respective chemical formulas (I) to (V) being shown below) to be used in the present invention can be obtained by synthesis, but are preferably obtained from an extract of the whole, or a leaf, flower, twig, root or fruit part of a plant belonging to the family Myrsinaceae, genus *Myrsine*. Examples of the plant belonging to the family Myrsinaceae include genus *Myrsine* containing the myrsinoic acids, taimin-tachibana that is a shrub native in middle to southern Japan and a tropical zone. Taimin-tachibana also referred to as hichinoki or sogeki has scientific names *Myrsine seguinii* and *Rapanaea neriifolia*.

Since the fruit of *Myrsine seguinii* has been traditionally eaten, there is no concern about its safety. As especially preferable parts for extraction, leaf and fruit may be named, because their production masses are large and the extraction rates can be high.

Myrsinoic acid A:

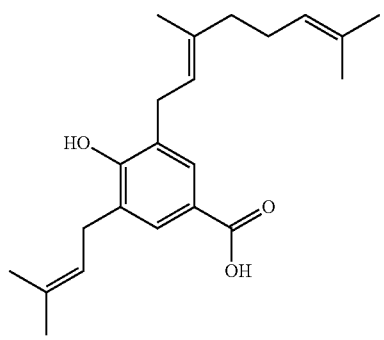

(I)

Myrsinoic acid B:

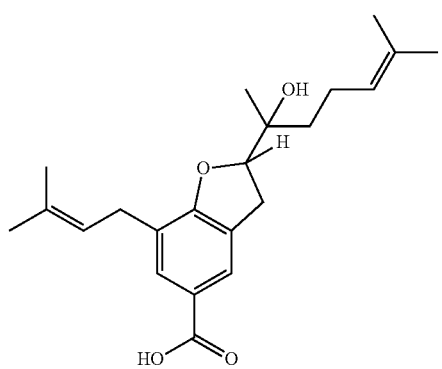

(II)

Myrsinoic acid C:

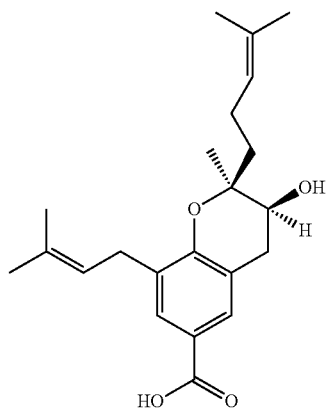

(III)

Myrsinoic acid E:

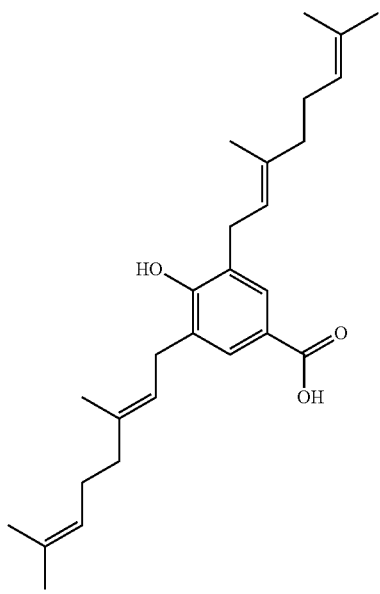

(IV)

Myrsinoic acid F:

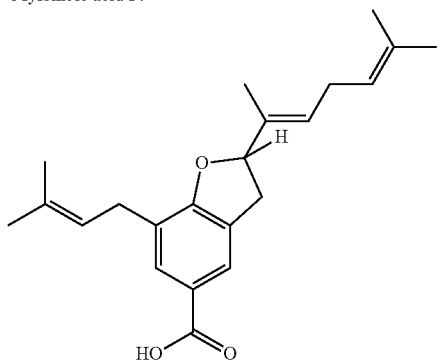

(V)

Myrsinoic acids have very high inhibitory activity, and among them myrsinoic acid B can be exemplified as an especially preferable type due to its strong methioninase inhibitory activity and a high content in the extract.

Although there is no particular restriction on a preparation method for the plant extraction according to the present invention and a conventionally known method can be applicable, the plant is generally first crushed by an appropriate means. Then extraction is conducted according to a conventional extraction method using a mixed solvent of one or more of water, lower alcohols, such as methanol, ethanol, n-propanol, and n-butanol, organic solvents, such as ether, chloroform, ethyl acetate, acetone, glycerin and propylene glycol. However, since the present invention is directed to a medicament, an oral composition and a food or drink, as an extraction solvent a combination of water and ethanol is preferable in view of the safety. Although extraction any of at a higher temperature, at room temperature and a lower temperature is possible, preferable extraction conditions are approximately at 50 to 80° C. and for 1 to 5 hours.

The thus obtained extract may be filtered, concentrated under a reduced pressure or freeze-dried before use. The extract may be separated and purified to obtain myrsinoic acids by a publicly known means for separation and purification, such as adsorption chromatography, partition chromatography, high performance liquid chromatography and thin-layer chromatography. More specifically, the extract is subjected to a liquid-liquid extraction, to silica gel column chromatography with an ethyl acetate/hexane mixed solvent, and further to octadecyl silylated column chromatography with a methanol/water (85%) mixed solvent containing additionally 0.1% acetic acid to obtain high purity myrsinoic acids by elution, fraction, concentration and drying.

The methioninase inhibitor of the present invention can be prepared by using as an active ingredient the myrsinoic acids and an extract of a plant belonging to the family Myrsinaceae, genus *Myrsine*, for example an extract of *Myrsine seguinii*, prepared as above. As necessary the ingredient may be dissolved or dispersed in an appropriate liquid vehicle, or mixed with an appropriate powder carrier or adsorbed thereon, and according to need mixed additionally with an emulsifier, a stabilizer or a dispersant to be formulated to a tablet, a powder, an emulsion, a water-dispersible powder, etc. The content of the dry extract with respect to the total formulation is preferably 0.001 to 50% by weight, and more preferably 0.01 to 25% by weight.

Since the methioninase inhibitor of the present invention is superior in fragrance, taste and safety, it can be mixed and consumed routinely in an oral composition, such as a tooth paste, a mouthwash and a deodorant spray, confections, such as a chewing gum, a candy, a tablet candy, a gummy jelly, a chocolate and a biscuit, frozen desserts, such as an ice cream, a sherbet and a water ice, foods or drinks, such as beverages, soup and jam. The content of the dry extract in the food or drink, or composition is about 0.001% by weight or more, and preferably about 0.01% by weight or more. In case of the food or drink, it is favorable to add the same to the content of about 0.001 to 5% by weight, and preferably about 0.01 to 1% by weight considering the taste.

The product of the present invention will be described in more detail by means of test examples, provided that they should not be interpreted in any restrictive way concerning the scope of the product of the present invention.

Test Example 1

This test was conducted to prepare a myrsinoic acid, an extract of *Myrsine seguinii* and comparative various plant extracts.
1) Test Samples
*Myrsine seguinii*, and for comparison a whole grass dry powder of Iceland moss, an alkanet root, a guava leaf, and green tea were used.
2) Test Method
Each of plant extracts and myrsinoic acids were prepared as described below, provided that the present invention be not limited thereto.

(1) Sample Preparation Example 1

Preparation of Extracts by Water

To 5 g of a dry powder leaf of *Myrsine seguinii*, 50 mL of water was added for extraction at 70° C. for 2 hours. The obtained extract liquid was filtered and freeze-dried to obtain 0.75 g of an extract.

Similarly a twig and a fruit of *Myrsine seguinii* were extracted respectively by water, and the extract liquids were concentrated or freeze-dried to prepare the extracts. The yields of the extracts are shown in Table 1.

(2) Sample Preparation Example 2

Preparation of Extracts by 25% Ethanol

To 5 g of a dry powder twig of *Myrsine seguinii,* 50 mL of 25% ethanol was added for extraction at 70° C. for 2 hours. The obtained extract liquid was filtered, the solvent was removed, and the residue was freeze-dried to obtain 0.80 g of an extract.

Similarly a leaf and a fruit of *Myrsine seguinii* were extracted respectively by 25% ethanol, and the extract liquids were concentrated or freeze-dried to prepare the extracts. The yields of the extracts are shown in Table 1.

(3) Sample Preparation Example 3

Preparation of Extracts by 50% Ethanol

To 5 g of a dry powder fruit of *Myrsine seguinii,* 50 mL of 50% ethanol was added for extraction at 70° C. for 2 hours. The obtained extract liquid was filtered, the solvent was removed, and the residue was freeze-dried to obtain 0.80 g of an extract.

Similarly a leaf and a twig of *Myrsine seguinii* were extracted respectively by 50% ethanol, and the extract liquids were concentrated or freeze-dried to prepare the extracts. The yields of the extracts are shown in Table 1.

(4) Sample Preparation Example 4

Preparation of Extracts by 75% Ethanol

To 5 g of a dry powder leaf of *Myrsine seguinii,* 50 mL of 75% ethanol was added for extraction at 70° C. for 2 hours. The obtained extract liquid was filtered, the solvent was removed, and the residue was freeze-dried to obtain 0.80 g of an extract.

Similarly a twig and a fruit of *Myrsine seguinii* were extracted respectively by 75% ethanol, and the extract liquids were concentrated or freeze-dried to prepare the extracts. The yields of the extracts are shown in Table 1.

(5) Sample Preparation Example 5

Preparation of Extracts by 100% Ethanol

To 5 g of a dry powder leaf of *Myrsine seguinii,* 50 mL of 100% ethanol was added for extraction at 70° C. for 2 hours. The obtained extract liquid was filtered, and freeze-dried to obtain 0.45 g of an extract.

Similarly a twig and a fruit of *Myrsine seguinii* were extracted respectively by 100% ethanol, and the extract liquids were concentrated or freeze-dried to prepare the extracts. The yields of the extracts are shown in Table 1.

(6) Sample Preparation Example 6

Preparation of Extracts by Acetone

To 5 g of a dry powder fruit of *Myrsine seguinii,* 50 mL of acetone was added for extraction at 70° C. for 2 hours. The obtained extract liquid was filtered, the solvent was removed, and the residue was freeze-dried to obtain 0.40 g of an extract.

Similarly a leaf and a twig of *Myrsine seguinii* were extracted respectively by acetone, and the extract liquids were concentrated or freeze-dried to prepare the extracts. The yields of the extracts are shown in Table 1.

(7) Sample Preparation Example 7

Preparation of Myrsinoic Acids

A 1% aqueous solution of the extract of a leaf of *Myrsine seguinii* by 100% ethanol was solvent-fractionated three times with the same volume of hexane, and the solvent was removed by distillation to obtain the hexane fractions (yield about 20%). The hexane fractions were subjected to silica gel column chromatography using a mixed solvent of ethyl acetate/hexane (10 to 20%) to separate about 20% of non-polar components to obtain a fraction containing myrsinoic acids (yield about 40%). This fraction was subjected to octadecyl silylated column chromatography using 0.1% acetic acid added methanol/water (85%) for elution and separation to obtain 400 mg of myrsinoic acid B and 100 mg of myrsinoic acid C.

Similarly, the hexane fractions were subjected to silica gel column chromatography and octadecyl silylated column chromatography for fractionation to obtain 60 mg of myrsinoic acid A, 3 mg of myrsinoic acid E and 1.5 mg of myrsinoic acid F.

(8) Sample Preparation Example 8

Synthesis of Myrsinoic Acid

Myrsinoic acid E was obtained by hydrolysis of a methyl ester prepared from 2-iodophenol by geranylation and carbonylation according to the method of Proceedings of Symposium on the Chemistry of Terpenes, Essential Oils, and Aromatics, Vol. 46, 396-398 (2002).

(9) Comparative Sample Preparation Example

To 5 g of a dry powder whole grass of Iceland moss, 50 mL of 50% ethanol was added for extraction at 70° C. for 2 hours. The obtained extract liquid was filtered, the solvent was removed, and the residue was freeze-dried to obtain 1.10 g of an extract.

Similarly an alkanet root, a guava leaf and green tea were extracted respectively by 50% ethanol, and the extract liquids were concentrated or freeze-dried to prepare the extracts.

3) Test Results

The yields of the extracts are shown in Table 1.

TABLE 1

Extraction examples of products of the present invention and comparative products

| Plant name | Extraction solvent | Extraction yield (%) | Part |
|---|---|---|---|
| *Myrsine seguinii* | 100% Ethanol | 9 | Leaf |
|  | 75% Ethanol | 16 |  |
|  | 50% Ethanol | 19 |  |
|  | 25% Ethanol | 19 |  |
|  | Water | 15 |  |
|  | 100% Ethanol | 5 | Twig |
|  | 75% Ethanol | 14 |  |
|  | 50% Ethanol | 15 |  |
|  | 25% Ethanol | 16 |  |
|  | Water | 13 |  |
|  | 100% Ethanol | 10 | Fruit |
|  | 75% Ethanol | 15 |  |

TABLE 1-continued

Extraction examples of products of the present
invention and comparative products

| Plant name | Extraction solvent | Extraction yield (%) | Part |
|---|---|---|---|
| | 50% Ethanol | 16 | |
| | 25% Ethanol | 16 | |
| | Water | 13 | |
| | Acetone | 8 | |
| Iceland moss | 50% Ethanol | 22 | Whole grass |
| Alkanet | 50% Ethanol | 6 | Root |
| Guava | 50% Ethanol | 22 | Leaf |
| Green tea | 50% Ethanol | 24 | Leaf |

Test Example 2

This test was conducted to examine the methioninase inhibitory activity of myrsinoic acids and the *Myrsine seguinii* extract.

1) Test Samples

The *Myrsine seguinii* extract and myrsinoic acids, as well as for comparison extracts of the whole grass dry powder of Iceland moss, the alkanet root, the guava leaf, and the green tea prepared in Test Example 1 were used.

2) Test Method (Cell-Free Methioninase Inhibition Test)

Methyl mercaptan, ammonia and α-ketobutyrate are produced from methionine by a reaction according to the methioninase. The production amount of α-ketobutyrate that is a considerably stable compound among the reaction products was used as an index of the enzyme reaction.

More specifically, *Fusobacterium nucleatum* JCM 8532 was cultured for 2 days under an anaerobic condition and disrupted by sonication to obtain the enzyme (final concentration: 300 μg-protein/mL), which was then mixed with methionine (final concentration: 30 mM), pyridoxal phosphate (final concentration: 50 μM), and the sample (final concentration: 200 μg/mL) in a phosphate buffer solution (50 mM, pH 7.6). After incubation at 37° C. for 1 hour, 1 mL of the reaction liquid was mixed with a ½ volume of an aqueous solution of perchloric acid (6%) to degenerate the proteins and the mixture was centrifuged at 3000×g for 10 min for separating the precipitates to obtain the sample liquid. In order to quantify the reaction byproduct of α-ketobutyrate, to 0.4 mL of the sample liquid were added 0.4 mL of a 0.05% 3-methyl-2-benzothiazolinonehydrazone (MBTH) solution and 0.8 mL of a 1 M sodium acetate buffer solution (pH 5.0), and the mixture was reacted at 50° C. for 30 min. After the reaction and confirming that the temperature of the reaction liquid was cooled down to room temperature, the absorbance (335 nm) was measured.

Since the color of the sample to be evaluated may have some influence on the result of the quantification reaction of α-ketobutyrate, the absorbance was corrected using a blank sample (a reaction liquid of the aforedescribed reaction except that methionine is excluded), which value was deducted for compensation.

The amount of α-ketobutyrate was determined using a calibration curve prepared in advance, and an inhibition rate was calculated according to the following formula:

Inhibition rate (%) = $((C-S)/C) \times 100$ wherein C is the amount of α-ketobutyrate in the control, and S is the amount of α-ketobutyrate when the sample is added.

3) Test Results

The measurement results of the methioninase inhibitory activity are shown in Table 2. For comparison, the extract of the whole grass dry powder of Iceland moss, the extract of the alkanet root, the extract of the guava leaf, and the extract of the green tea (see e.g. Japanese Patent Application Laid-Open No. 2003-26527), whose inhibitory activities against methioninase originated from oral bacterium (*Fusobacterium nucleatum*) have been known, were also evaluated. The respective inhibition rates were 29% for the extract of the whole grass dry powder of Iceland moss, 28% for the extract of the alkanet root, 22% for the extract of the guava leaf, and 26% for the extract of the green tea.

The extracts of a leaf, a twig and a fruit of *Myrsine seguinii* of the present invention exhibited respectively high inhibitory activities against methioninase. The test results showed that the extracts of a leaf, a twig and a fruit of *Myrsine seguinii* of the present invention have strong inhibitory activities against methioninase.

As shown in Table 3, myrsinoic acids A, B, C, E, and F inhibited methioninase by 50% at a concentration of 5 μg/mL or less. Consequently an isolated myrsinoic acid has strong inhibitory activity, indicating that the same is the active ingredient contained in the *Myrsine seguinii* extract.

TABLE 2

Inhibitory activities against methioninase of products of
the present invention and comparative products

| Plant name | Extraction solvent | Inhibition rate (%) | Part |
|---|---|---|---|
| *Myrsine seguinii* | 100% Ethanol | 100 | Leaf |
| | 75% Ethanol | 100 | |
| | 50% Ethanol | 100 | |
| | 25% Ethanol | 100 | |
| | Water | 24 | |
| | 100% Ethanol | 100 | Twig |
| | 75% Ethanol | 100 | |
| | 50% Ethanol | 100 | |
| | 25% Ethanol | 100 | |
| | Water | 78 | |
| | 100% Ethanol | 100 | Fruit |
| | 75% Ethanol | 100 | |
| | 50% Ethanol | 100 | |
| | 25% Ethanol | 100 | |
| | Water | 50 | |
| | Acetone | 100 | |
| Iceland moss | 50% Ethanol | 29 | Whole grass |
| Alkanet | 50% Ethanol | 28 | Root |
| Guava | 50% Ethanol | 22 | Leaf |
| Green tea | 50% Ethanol | 26 | Leaf |

TABLE 3

Inhibitory activities ($IC_{50}$) against methioninase
of products of the present invention and
comparative products

| Sample | $IC_{50}$ (μg/ml) |
|---|---|
| Extract of *Myrsine seguinii* by 100% ethanol | 30 |
| Myrsinoic acid A | 5 |
| Myrsinoic acid B | 4 |
| Myrsinoic acid C | 5 |
| Myrsinoic acid E | 5 |
| Myrsinoic acid F | 3 |
| Myrsinoic acid E (Synthesized) | 5 |
| Green tea Extract of green tea by 50% ethanol | 200 |

Test Example 3

This test was conducted to examine the inhibitory activity against methioninase of living bacteria by myrsinoic acids and the *Myrsine seguinii* extract.

1) Test Samples

The *Myrsine seguinii* extract, as well as for comparison extracts of the whole grass dry powder of Iceland moss, the alkanet root, the guava leaf, and the green tea prepared in Test Example 1 were used.

2) Test Method (Inhibition Test Against Methioninase of Living Bacteria)

In order to evaluate an odor eliminating activity under conditions closer to human intraoral conditions, *Fusobacterium nucleatum* JCM8532 cultured for about 16 hours under an anaerobic condition was centrifuged and suspended in a physiological saline buffer solution (40 mM phosphate buffer/50 mM sodium chloride, pH 7.7) to obtain a living bacterial suspension (10% of a reaction system), which was then reacted with methionine (final concentration: 1 mM) and the sample (final concentration: 1 to 200 μg/mL) in a physiological saline buffer solution at 37° C. for 90 min. Then 0.5 mL of the head-space gas was analyzed by gas chromatography.

3) Test Results

The results are shown in Table 4. The green tea extract was evaluated as a comparative sample, which inhibition rate was 66%. The extracts of a *Myrsine seguinii* leaf of the present invention exhibited a high inhibitory activity against methioninase at a lower concentration.

TABLE 4

Inhibitory activities against methioninase of living bacteria by product of the present invention and comparative product

| Sample | Concentration (μg/mL) | Inhibition rate (%) |
|---|---|---|
| Extract of *Myrsine seguinii* leaf by 100% ethanol | 200 | 100 |
|  | 100 | 86 |
|  | 50 | 83 |
|  | 25 | 55 |
|  | 10 | 24 |
|  | 1 | 10 |
| Extract of green tea by 50% ethanol | 200 | 66 |

The present invention will now be described in more detail by way of examples thereof, provided that the examples should not be interpreted in any restrictive way concerning the scope of the present invention.

Using a product of the present invention prepared by a method described in Sample Preparation Examples 1 to 7, compositions, such as a tooth paste, a mouthwash, a deodorant spray, a breath spray, a tablet and a powder; and confections, such as a chewing gum, a candy, a tablet candy, a gummy jelly, a chocolate and a biscuit, frozen desserts, such as an ice cream, a sherbet and a water ice, foods or drinks, such as beverage, soup and jam were produced.

Example 1

Formulation of Tooth Paste

Calcium carbonate (50.0% by weight)
Glycerin (20.0)
Carboxymethylcellulose (2.0)
Sodium lauryl sulfate (2.0)
Perfume (1.0)
Saccharin (0.1)
Extract of *Myrsine seguinii* fruit by water in Sample Preparation Example 1 (1.0)
Chlorhexidine (0.01)
Water (balance)
Total (100.0)

Example 2

Formulation of Mouthwash

Ethanol (2.0% by weight)
Perfume (1.0)
Saccharin (0.05)
Chlorhexidine hydrochloride (0.01)
Extract of *Myrsine seguinii* twig by 25% ethanol in Sample Preparation Example 2 (0.5)
Water (balance)
Total (100.0)

Example 3

Formulation of Deodorant Spray

Ethanol (49.5% by weight)
Extract of *Myrsine seguinii* fruit by 50% ethanol in Sample Preparation Example 3 (0.5)
Water (50.0)
Total (100.0)
The mixture was filled in an aerosol container together with a propellant gas (nitrogen gas) to prepare a deodorant spray.

Example 4

Formulation of Breath Spray

Ethanol (10.0% by weight)
Glycerin (5.0)
Extract of *Myrsine seguinii* leaf by 50% ethanol in Sample Preparation Example 3 (1.0)
Perfume (0.05)
Colorant (0.001)
Water (balance)
Total (100.0)

Example 5

Formulation of Lozenge

Dextrose (72.3% by weight)
Lactose (19.0)
Gum arabic (6.0)
Perfume (1.0)
Sodium monofluorophosphate (0.7)
Extract of *Myrsine seguinii* fruit by 75% ethanol in Sample Preparation Example 4 (1.0)
Total (100.0)

Example 6

Formulation of Chewing Gum

Gum base (20.0% by weight)
Sugar (55.0)
Glucose (15.0)
Glutinous starch syrup (9.0)
Perfume (0.5)
Extract of *Myrsine seguinii* leaf by 100% ethanol in Sample Preparation Example 5 (0.5)
Total (100.0)

Example 7

Formulation of Candy

Sugar (50.0% by weight)
Glutinous starch syrup (34.0)
Perfume (0.5)
Extract of *Myrsine seguinii* fruit by acetone in Sample Preparation Example 6 (0.5)
Water (balance)
Total (100.0)

Example 8

Formulation of Tablet Candy

Sugar (76.4% by weight)
Glucose (19.0)
Sucrose fatty acid ester (0.2)
Perfume (0.2)
Extract of *Myrsine seguinii* twig by water in Sample Preparation Example 1 (0.1)
Water (balance)
Total (100.0)

Example 9

Formulation of Gummy Jelly

Gelatin (60.0% by weight)
Glutinous starch syrup (23.0)
Sugar (8.5)
Vegetable fat and oil (4.5)
Mannitol (2.95)
Lemon fruit juice (1.0)
Extract of *Myrsine seguinii* leaf by 25% ethanol in Sample Preparation Example 2 (0.05)
Total (100.0)

Example 10

Formulation of Chocolate

Powder sugar (39.8% by weight)
Cacao bitter (20.0)
Whole milk powder (20.0)
Cocoa butter (17.0)
Mannitol (2.0)
Extract of *Myrsine seguinii* fruit by 50% ethanol in Sample Preparation Example 3 (1.0)
Perfume (0.2)
Total (100.0)

Example 11

Formulation of Biscuit

Weak flour class 1 (25.59% by weight)
All-purpose flour class 1 (22.22)
Refined sugar (4.8)
Cooking salt (0.73)
Dextrose (0.78)
Palm shortening (11.78)
Sodium bicarbonate (0.17)
Sodium bisulfite (0.16)
Rice flour (1.45)
Whole milk powder (1.16)
Milk substitute powder (0.29)
Extract of *Myrsine seguinii* twig by 75% ethanol in Sample Preparation Example 4 (0.5)
Water (balance)
Total (100.0)

Example 12

Formulation of Ice Cream

Skim milk powder (50.0% by weight)
Cream (25.0)
Sugar (10.0)
Yolk (10.0)
Myrsinoic acid B in Sample Preparation Example 7 (0.1)
Perfume (0.1)
Water (balance)
Total (100.0)

Example 13

Formulation of Sherbet

Orange fruit juice (25.0% by weight)
Sugar (25.0)
Albumen (10.0)
Myrsinoic acid A in Sample Preparation Example 7 (0.2)
Water (balance)
Total (100.0)

Example 14

Formulation of Drink

Orange fruit juice (30.0% by weight)
Isomerized sugar (15.24)
Citric acid (0.1)
Vitamin C (0.04)
Perfume (0.1)
Myrsinoic acid C in Sample Preparation Example 7 (0.1)
Water (balance)
Total (100.0)

Example 15

Formulation of Soup

Milk (60.00% by weight)
Onion (20.00)
Carrot (10.00)
Vegetable stock (1.00)

Butter (0.10)
Pepper (0.05)
Cooking salt (0.05)
Myrsinoic acid E in Sample Preparation Example 7 (0.01)
Water (balance)
Total (100.0)

Example 16

Formulation of Jam

Fruit flesh (4.0% by weight)
Sugar (65.0)
Clear fruit juice (25.0)
Citric acid (0.5)
Myrsinoic acid F in Sample Preparation Example 7 (0.02)
Water (balance)
Total (100.0)

Example 17

Formulation of Tooth Paste

Calcium carbonate (50.0% by weight)
Glycerin (20.0)
Carboxymethylcellulose (2.0)
Sodium lauryl sulfate (2.0)
Perfume (1.0)
Saccharin (0.1)
Myrsinoic acid B in Sample Preparation Example 7 (0.1)
Myrsinoic acid C in Sample Preparation Example 7 (0.01)
Chlorhexidine (0.01)
Water (balance)
Total (100.0)

Example 18

Formulation of Deodorant Spray

Ethanol (49.5% by weight)
Myrsinoic acid B in Sample Preparation Example 7 (0.05)
Water (50.45)
Total (100.0)
The mixture was filled in an aerosol container together with a propellant gas (nitrogen gas) to prepare a deodorant spray.

Example 19

Formulation of Breath Spray

Ethanol (10.0% by weight)
Glycerin (5.0)
Myrsinoic acid B in Sample Preparation Example 7 (0.1)
Myrsinoic acid E in Sample Preparation Example 7 (0.01)
Perfume (0.05)
Colorant (0.001)
Water (balance)
Total (100.0)

Example 20

Formulation of Chewing Gum

Gum base (20.0% by weight)
Sugar (55.0)
Glucose (15.0)
Glutinous starch syrup (9.0)
Perfume (0.5)
Myrsinoic acid A in Sample Preparation Example 7 (0.01)
Myrsinoic acid B in Sample Preparation Example 7 (0.1)
Total (100.0)

Example 21

Formulation of Candy

Sugar (50.0% by weight)
Glutinous starch syrup (34.0)
Perfume (0.5)
Myrsinoic acid B in Sample Preparation Example 7 (0.05)
Myrsinoic acid F in Sample Preparation Example 7 (0.005)
Water (balance)
Total (100.0)

Example 22

Formulation of Tablet Candy

Sugar (76.4% by weight)
Glucose (19.0)
Sucrose fatty acid ester (0.2)
Perfume (0.2)
Myrsinoic acid A in Sample Preparation Example 7 (0.01)
Myrsinoic acid E in Sample Preparation Example 7 (0.001)
Water (balance)
Total (100.0)

Example 23

Formulation of Tablet

Myrsinoic acid B in Sample Preparation Example 7 (0.5% by weight)
Lactose (70.0)
Crystalline cellulose (15.0)
Magnesium stearate (5.0)
Total (100.0)
The components were finely milled, mixed and formed into tablets by a direct tableting method. The total weight of each tablet is 100 mg and the active ingredient therein is 10 mg.

Example 24

Formulation of Powder

Myrsinoic acid C in Sample Preparation Example 7 (0.05% by weight)
Corn starch (59.05)
Carboxycellulose (40.0)
Total (100.0)
The components were finely milled and mixed to form powder. One hundred (100) mg of the powder was filled in a hard capsule to produce a capsule formulation.

Example 25

Formulation of Chewing Gum

Gum base (19.4% by weight)
Sugar (55.0)
Glucose (15.0)
Glutinous starch syrup (9.0)
Perfume (0.5)
Extract of *Myrsine seguinii* leaf by 75% ethanol in Sample Preparation Example 4 (1.0)

Myrsinoic acid B in Sample Preparation Example 7 (0.1)

Total (100.0)

Example 26

Formulation of Breath Spray

Ethanol (10.0% by weight)

Glycerin (5.0)

Extract of *Myrsine seguinii* leaf by water in Sample Preparation Example 1 (1.1)

Myrsinoic acid B in Sample Preparation Example 7 (0.01)

Myrsinoic acid C in Sample Preparation Example 7 (0.01)

Perfume (0.05)

Colorant (0.001)

Water (balance)

Total (100.0)

Example 27

Formulation of Candy

Sugar (50.0% by weight)

Glutinous starch syrup (34.0)

Perfume (0.5)

Myrsinoic acid E in Sample Preparation Example 9 (0.05)

Water (balance)

Total (100.0)

The invention claimed is:

1. A method to reduce production of methyl mercaptan, the method comprising:

administering a composition comprising a methioninase inhibitor including as an active ingredient an extract of a plant belonging to family Myrsinaceae, genus *Myrsine* wherein the plant is *Myrsine seguinii*.

2. The method according to claim 1, wherein the composition is applied topically.

3. The method according to claim 2, wherein the composition is an oral composition.

4. The method according to claim 3, wherein the oral composition is a toothpaste, mouthwash, spray, confection, or gum.

5. The method according to claim 1, wherein the composition is ingested as a food or drink.

6. A method to reduce production of methyl mercaptan, the method comprising:

administering a composition comprising a methioninase inhibitor including as an active ingredient one or more selected from the group consisting of myrsinoic acid A, myrsinoic acid B, myrsinoic acid C, myrsinoic acid E and myrsinoic acid F according to the following formulas (I), (II), (III), (IV), and (V), respectively.

Myrsinoic acid A:

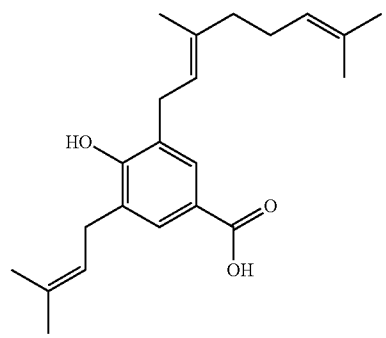

(I)

Myrsinoic acid B:

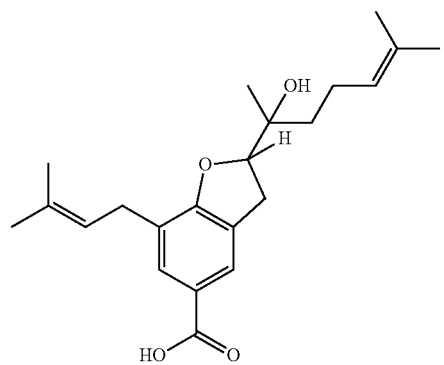

(II)

Myrsinoic acid C:

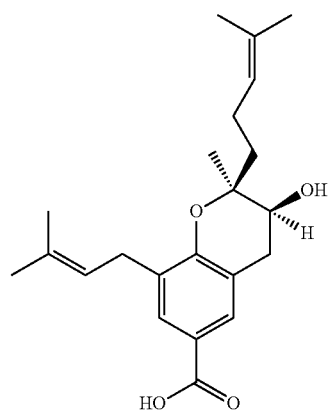

(III)

14. The method according to claim 13, wherein the extract comprises one or more compounds selected from the group consisting of myrsinoic acid A, myrsinoic acid B, myrsinoic acid C, myrsinoic acid E and myrsinoic acid F according to the following formulas (I), (II), (III), (IV), and (V), respectively.

Myrsinoic acid A:

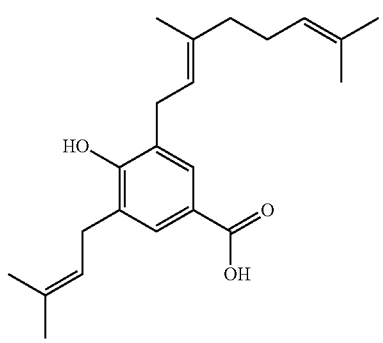

(I)

Myrsinoic acid B:

(II)

Myrsinoic acid C:

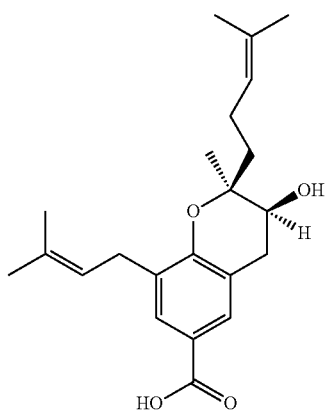

(III)

Myrsinoic acid E:

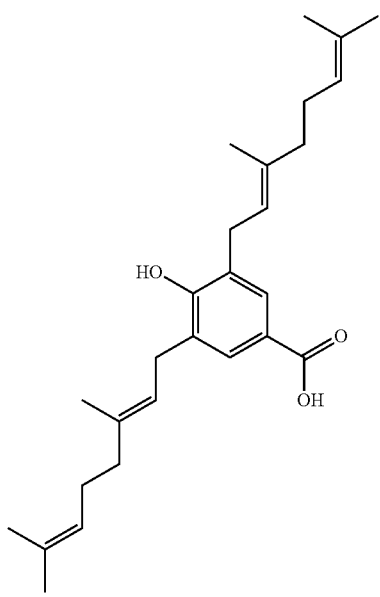

(IV)

Myrsinoic acid F:

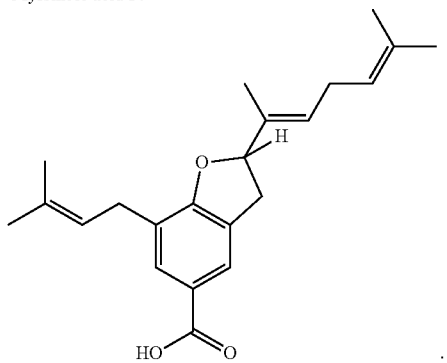

(V)

7. The method according to claim 6, wherein the myrsinoic acid A, myrsinoic acid B, myrsinoic acid C, myrsinoic acid E and myrsinoic acid F are extracted from a plant belonging to family Myrsinaceae, genus *Myrsine*.

8. The method according to claim 7, wherein the plant belonging to family Myrsinaceae, genus *Myrsine* is *Myrsine seguinii*.

9. The method according to claim 6, wherein the composition is applied topically.

10. The method according to claim 9, wherein the composition is an oral composition.

11. The method according to claim 10, wherein the oral composition is a toothpaste, mouthwash, spray, confection, or gum.

12. The method according to claim 6, wherein the composition is ingested as a food or drink.

13. A method of producing a composition configured to reduce production of methyl mercaptan, the method comprising:
mixing a methioninase inhibitor with an excipient, the excipient being configured to aid in a topical administration of the methioninase inhibitor, wherein
the methioninase inhibitor includes as an active ingredient an extract of a plant belonging to family Myrsinaceae, genus *Myrsine* wherein the plant is *Myrsine seguinii*.

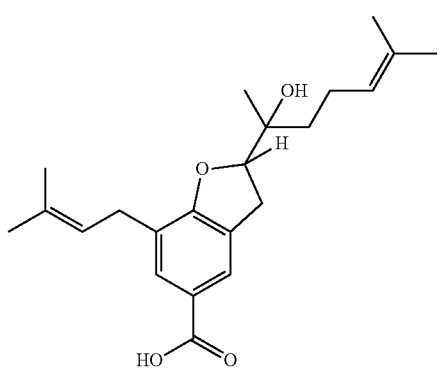

Myrsinoic acid E:
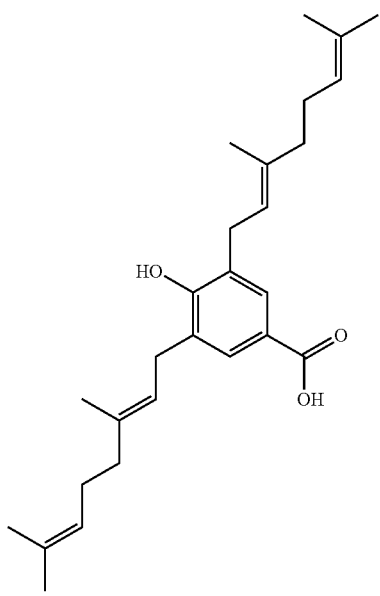
(IV)
Myrsinoic acid F:
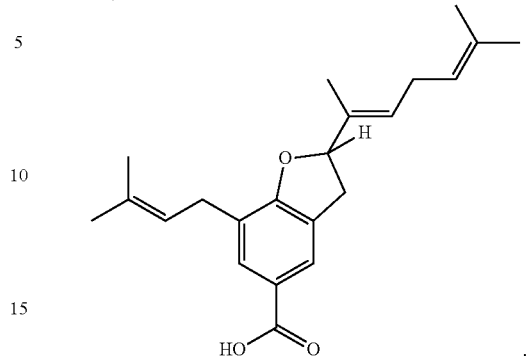
(V)
15. The method according to claim 13, wherein the excipient includes an oral composition.
16. The method according to claim 13, wherein the oral composition is a toothpaste, mouthwash, spray, confection, or gum.
* * * * *